US008546339B2

(12) United States Patent
Dal Farra et al.

(10) Patent No.: US 8,546,339 B2
(45) Date of Patent: *Oct. 1, 2013

(54) SOOTHING COSMETIC OR PHARMACEUTICAL COMPOSITION COMPRISING A PEPTIDE WHICH ACTIVATES HMG-COA REDUCTASE

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 141 days.

This patent is subject to a terminal disclaimer.

(21) Appl. No.: 13/141,338

(22) PCT Filed: Dec. 23, 2009

(86) PCT No.: PCT/FR2009/001478
§ 371 (c)(1),
(2), (4) Date: Jun. 22, 2011

(87) PCT Pub. No.: WO2010/072929
PCT Pub. Date: Jul. 1, 2010

(65) Prior Publication Data
US 2012/0014886 A1  Jan. 19, 2012

(30) Foreign Application Priority Data
Dec. 23, 2008 (FR) ...................... 08 07366

(51) Int. Cl.
| A61K 38/08 | (2006.01) |
| A61K 38/07 | (2006.01) |
| A61K 38/06 | (2006.01) |
| A61K 8/00 | (2006.01) |
| C07K 7/06 | (2006.01) |
| C07K 7/00 | (2006.01) |
| C07K 5/10 | (2006.01) |
| C07K 5/08 | (2006.01) |

(52) U.S. Cl.
USPC ....... 514/21.6; 514/18.8; 514/21.7; 514/21.8; 514/21.9; 530/328; 530/329; 530/330; 530/331

(58) Field of Classification Search
None
See application file for complete search history.

(56) References Cited

U.S. PATENT DOCUMENTS
| 8,053,003 | B2 | 11/2011 | Msika et al. | |
| 8,147,883 | B1 | 4/2012 | Msika et al. | |
| 2003/0060399 | A1* | 3/2003 | Brophy et al. | ...... 514/7 |
| 2008/0268077 | A1 | 10/2008 | Vielhaber | |

FOREIGN PATENT DOCUMENTS
| EP | 0738510 | 10/1996 |
| EP | 1272148 | 6/2006 |
| EP | 1707189 | 10/2006 |
| FR | 2789312 | 8/2000 |
| FR | 2868309 | 10/2005 |
| WO | 2004/058282 | 7/2004 |
| WO | 2005/060683 | 7/2005 |
| WO | 2007/068998 | 6/2007 |

OTHER PUBLICATIONS

Definition of derivative from http://cancerweb.ncl.ac.uk/omd/about.html, pp. 1-5. Accessed Jul. 7, 2005.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Schinzel R, Drueckes P, "The phosphate recognition site of *Escherichia coli* maltodextrin phosphorylase," FEBS, Jul. 1991, 286(1,2): 125-128.*
PCT, International Search Report, International Application No. PCT/FR2009/001478 (mailed May 6, 2010; published Jul. 1, 2010).
Gruszecka, M. et al., "Synthesis of peptides as potential antiviral agents against human rhinovirus 14," *Peptides* (1998), pp. 656-657; Proceedings of the European Peptide Symposium, 25th, Budapest, Aug. 30-Sep. 4, 1998.
PCT, International Preliminary Report on Patentability, International Application No. PCT/FR2009/001478 (Jul. 5, 2011).
Ghadially, R. et al., "The Aged Epidermal Permeability Barrier," *The Journal of Clinical Investigations, Inc.*, vol. 95, pp. 2281-2290 (May 1995).
Kullmann, W., "Proteases as Catalysts for Enzymic Synthesis of Opiod Peptides," *The Journal of Biological Chemistry*, vol. 255, No. 17, pp. 8234-8238 (Sep. 1980).
Luskey, K.L. et al., "Human 3-Hydroxy-3-methylglutaryl Coenzyme A Reductase," *The Journal of Biological Chemistry*, vol. 260, No. 18, pp. 10271-01277 (Aug. 1985).

(Continued)

Primary Examiner — Julie Ha
(74) Attorney, Agent, or Firm — Thompson Hine L.L.P.

(57) ABSTRACT

Soothing cosmetic or pharmaceutical composition that includes at least one peptide as an active principle that activates human HMG-CoA reductase of general formula (I): $R_1\text{-}(AA)_n\text{-}X_1\text{-}Gly\text{-}Lys\text{-}X_2\text{-}(AA)_p\text{-}R_2$ and is chosen from among sequences SEQ ID NO: 1 to SEQ ID NO: 10, in a physiologically suitable medium is described. This novel peptide is designed to act as a soothing active principle capable of providing a solution to skin sensitivity in a cosmetic composition. The invention further applies to a cosmetic treatment method intended to combat skin irritations.

18 Claims, No Drawings

(56) References Cited

OTHER PUBLICATIONS

Martini, M.C., "Biochemical analysis of epidermal lipids," *Pathologie Biologie*, vol. 51, pp. 267-270 (2003).

Menon, G.K. et al., "De novo sterologenesis in the skin. II. Regulation by cutaneous barrier requirements," *Journal of Lipid Research*, vol. 26, pp. 418-427 (1985).

Norlén, L. et al., "Inter- and Intra-Individual Differences in Human Stratum Corneum Lipid Content Related to Physical Parameters of Skin Barrier Function In Vivo," *The Journal of Investigative Dermatology*, vol. 112, No. 1, pp. 72-77.

Proksch, E. et al., "Barrier function regulates epidermal lipid and DNA synthesis," *British Journal of Dermatology*, vol. 128, pp. 473-482 (1993).

\* cited by examiner

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Glu Gly Lys Gly Lys Ser Val Val Cys Glu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Glu Gly Lys Gly Lys Ser Val Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 3

Asp Gly Lys Gly Lys Thr
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Arg Gly Lys Ser
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 5

Arg Gly Lys Ser
1
```

```
<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Arg Gly Lys Thr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 7

Arg Gly Lys Thr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Lys Gly Lys Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 9

Lys Gly Lys Ser
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: AMIDATION

<400> SEQUENCE: 10

Gly Lys Ser
1
```

SOOTHING COSMETIC OR PHARMACEUTICAL COMPOSITION COMPRISING A PEPTIDE WHICH ACTIVATES HMG-COA REDUCTASE

The present invention is situated in the cosmetic and pharmaceutical field, and more particularly in the dermatology field. The present invention relates to a cosmetic or pharmaceutical composition comprising, as an active principle, at least one peptide that activates human HMG-CoA reductase of general formula (I)

$R_1$-$(AA)_n$-$X_1$-Gly-Lys-$X_2$-$(AA)_p$-$R_2$, and sequence SEQ ID No. 1 to SEQ ID No. 10, in a physiologically suitable medium.

The present invention further relates to the utilization of this novel peptide as a soothing active principle in a cosmetic composition.

The invention is also relative to the utilization of this novel active principle for producing a pharmaceutical composition, and particularly a dermatological composition, intended to prevent or treat cutaneous inflammation, such as erythema, in particular due to ultraviolet radiation, pruritus, urticaria, insect bites, allergies, or else alopecia in its inflammatory phases. The invention further applies to a cosmetic treatment process intended to prevent or combat cutaneous irritations, according to which an effective quantity of active principle, or a composition containing the active principle, is applied to the areas to be treated.

The first function of the epidermis is to constitute a barrier between the external environment and the internal environment. The outermost layer of the epidermis, the horny layer of the epidermis, ensures this function. It is composed of keratinocytes in the last stage of their differentiation, corneocytes, sealed to each other by thick intercellular lipid cement that is both flexible and impermeable. This lipid cement contains cholesterol, a neutral lipid actively synthesized by the keratinocytes from the intermediate layers of the epidermis. The membrane-bound enzyme that plays a key role in this synthesis is 3-hydroxy-3-methylglutaryl-Coenzyme A (HMG-CoA)-reductase (E.C. 1.1.1.34), that exists in at least two isoforms in human skin (Luskey et al., J Biol Chem., 1985 260(18), p. 10271-7).

Following a sudden alteration in the cutaneous barrier, a significant and rapid increase in cholesterol synthesis is observed, associated with an increase in the expression and activity of HMG-CoA reductase (Menon G. K. et al., J. Lipid, Res., 1985, (26), P. 418-427). On the other hand, drug-induced inhibition, by the topical administration of statins, confirms the importance of cholesterol in the epidermal barrier function and the central role of HMG-CoA reductase (Proksch E. et al., British J. Dermatol., 1993, (128), p. 473-482).

Many people suffer from symptoms connected to the high sensitivity of skin. This sensitivity most often is manifested in redness (erythema), pain, tingling or pruritus, or even the onset of reaction acne. The causes for the onset of this sensitivity are many, but sensitivities connected to stress, the absorption of certain foods, reactivity connected to climactic conditions or else secondary effects connected to the topical application of irritant products may be distinguished.

Most of the symptoms connected to skin sensitivity result from irritative processes that activate localized cellular reactions leading to the release of semiochemicals, such as cytokines, substance P or prostaglandins. Skin irritation is generally accompanied by an alteration in the barrier function.

The main objective of the present invention is to provide a novel soothing active principle, capable of providing a solution to skin sensitivity.

In order to soothe the sensations of discomfort of sensitive skin, first, the signs of the irritation, such as erythema and tingling, must be limited by slowing down the release of cellular inflammation mediators and, second, alterations in the barrier function of the epidermis must be prevented or the barrier function of the epidermis must be reestablished. In this particular domain, the direct supply of lipid substitutes, such as ceramides (EP 1272148, US2007576937) or certain cholesterol derivatives (FR 2 789 312) has largely been described. On the other hand, the utilization of polyphenols to limit the release of inflammation mediators has also been described (WO/2004/058282). However, to date, no document describes or suggests that a peptide that activates human HMG-CoA reductase may have interesting properties for soothing sensitive skin and for preventing or combating skin irritations.

In particular, it has been demonstrated that these peptides, when applied to the skin, protect the skin from various experimental irritants.

"Active principle that activates human HMG-CoA reductase" is understood to be any biologically active peptide or derivative capable of increasing HMG-CoA reductase activity, either by increasing the protein synthesis of HMG-CoA reductase (by direct or indirect modulation of the gene expression of HMG-CoA reductase), or by increasing the enzymatic activity of HMG-CoA reductase, or by other biological processes such as stabilization of the HMG-CoA reductase protein or else stabilization of messenger RNA transcripts.

"Skin" is understood to refer to all of the covering tissues of the organism, including the scalp and mucous membranes.

"Topical application" is understood to refer to the act of applying or spreading the active principle according to the invention, or a composition containing the principle, to or on the surface of the skin.

"Physiologically acceptable" is understood to mean that the active principle according to the invention, or a composition containing the principle, is appropriate for entering in contact with the skin without causing toxicity or intolerance reactions.

Thus, the object of the invention is a peptide that activates human HMG-CoA reductase.

The expression "peptide that activates human HMG-CoA reductase" designates any biologically active peptide fragment in which the amino acid sequence is partially or entirely analogous or homologous to the human HMG-CoA reductase peptide sequence.

The expression "biologically active" is understood to mean "has an in vivo or in vitro activity characteristic of the activity of the active principle according to the invention."

According to a particularly advantageous embodiment of the invention, the peptide has a sequence of general formula (I)

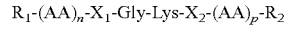

In which, $X_1$ is lysine or arginine or no amino acid,
$X_2$ is serine or threonine,
AA represents any amino acid, or one of its derivatives, and n and p are integers between 0 and 4,
$R_1$ represents the primary amine function of the N-terminal amino acid, free or substituted by a protecting group that may be chosen from among an acetyl group, a benzoyl group, a tosyl group or a benzyloxycarbonyle group, $R_2$ represents the hydroxyl group of the carboxyl function of the C-terminal amino acid, free or substituted by a protecting group that may be chosen from among an alkyl chain from $C_1$ to $C_{20}$, or an $NH_2$, NHY or NYY group with Y representing an alkyl chain from $C_1$ to $C_4$.

The peptide is characterized in that the peptide is chosen from among the following sequences:

```
                                         (SEQ ID No. 1)
Glu-Gly-Lys-Gly-Lys-Ser-Val-Val-Cys-Glu (SEQ ID No. 2)
Glu-Gly-Lys-Gly-Lys-Ser-Val-Val (SEQ ID No. 3)
Asp-Gly-Lys-Gly-Lys-Thr (SEQ ID No. 4)
Arg-Gly-Lys-Ser (SEQ ID No. 5)
Arg-Gly-Lys-Ser-NH2

(SEQ ID No. 6)
Arg-Gly-Lys-Thr (SEQ ID No. 7)
Arg-Gly-Lys-Thr-NH2

(SEQ ID No. 8)
Lys-Gly-Lys-Ser (SEQ ID No. 9)
Lys-Gly-Lys-Ser-NH2

(SEQ ID No. 10)
Gly-Lys-Ser-NH2
```

According to a particularly interesting embodiment, the biologically active peptide corresponds to the SEQ ID No. 4 sequence.

According to another particularly interesting embodiment, the biologically active peptide corresponds to the SEQ ID No. 5 sequence.

The invention also relates to homologous forms of these sequences. The term "homologous" designates, according to the invention, any peptide sequence identical to at least 50%, or preferably at least 80%, and still more preferentially to at least 90% of said peptide sequence, chosen from among the SEQ ID No. 1 to SEQ ID No. 10 sequences. "Peptide sequence identical to at least X %" is understood to designate a percentage identity between the amino acid residues of two sequences to be compared, obtained after the optimal alignment of the two sequences. The optimal alignment is obtained by using local homology algorithms such as those used by the BLAST P or T BLAST N computer software available on the NCBI site.

The term "homologous" may also designate a peptide that differs from the sequence of a peptide of SEQ ID No. 1 to SEQ ID No. 10 sequence by the substitution of chemically equivalent amino acids, i.e., by the substitution of a residue by another having the same characteristics. Thus, conventional substitutions take place between Ala, Val, Leu and Ile; between Ser and Thr; between the acid residues Asp and Glu; between Asn and Gln; and between the basic residues Lys and Arg; Or between the aromatic residues Phe and Tyr.

In the invention, the term "amino acid" here refers to any natural or non-natural organic acid having the formula:

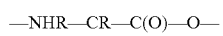

—NHR—CR—C(O)—O—

Where each —R is independently selected between a hydrogen and an alkyl group having between 1 and 12 carbon atoms. Preferentially, at least one —R group of each amino acid is a hydrogen. Here the term "alkyl" refers to a carbon chain that may be linear or branched, substituted (mono- or poly-) or non-substituted; Saturated, monosaturated (a double or triple bond in the chain) or polyunsaturated (two or more double bonds, two or more triple bonds, one or more double bonds and one or more triple bonds in the chain).

The term "peptide" designates a linkage of two or more amino acids interlinked by peptide linkages or by modified peptide linkages.

"Peptide" is also understood to refer to the natural or synthetic peptide of the invention as described above, or at least one of its fragments, whether obtained by proteolysis or synthetically, or else any natural or synthetic peptide whose sequence is partially or totally constituted by the sequence of the peptide previously described.

So as to improve resistance to degradation, it may be necessary to use a protected form of the peptide according to the invention. The form of protection must obviously be a biologically compatible form and must be compatible with a use in the field of cosmetics or pharmacy.

Many forms of biologically compatible protection may be contemplated. They are well known to the person skilled in the art as, for example, the acylation or acetylation of the amino terminal end, or the amidation or esterification of the carboxy terminal end. Thus, the invention relates to a composition such as previously defined, characterized by the fact that the peptide of SEQ ID No. 1 to SEQ ID No. 10 is in protected or unprotected form. Protection based on a substitution on the amino terminal end by an acetyl group, a benzoyl group, a tosyl group or a benzyloxycarbonyle group may be utilized. Preferably, protection based on the amidation of the hydroxyl function of the carboxy terminal end by an NYY group with Y representing an alkyl chain from $C_1$ to $C_4$, or the esterification by an alkyl group is utilized. It is also possible to protect the two ends of the peptide.

The peptide derivatives also relate to amino acids and peptides interconnected by a pseudo-peptidic linkage. "Pseudo-peptidic linkage" is understood to refer to all types of linkages capable of replacing "conventional" peptidic linkages.

In the domain of amino acids, the molecules have a geometry such that they may theoretically be present in the form of different optical isomers. Thus, there exists a molecular conformation of the amino acid (AA) that rotates the plane of polarized light to the right (dextrorotatory conformation or D-aa), and a molecular conformation of amino acid (aa) that rotates the plane of polarized light to the left (levorotatory conformation or L-aa). Natural amino acids are always of levorotatory conformation; consequently, a peptide of natural origin will only be constituted of L-aa type amino acids. However, chemical synthesis in laboratory enables amino acids with the two possible conformations to be prepared. From this base material, it is possible to incorporate, during peptide synthesis, amino acids in both dextrorotatory and levorotatory optical isomer forms. Thus, amino acids constituting the peptide according to the invention may be in L- and D-configurations; preferentially, the amino acids are in L form. The peptide according to the invention may thus be in L-, D- or DL-form.

The peptide of general formula (I) according to the invention may be obtained either by conventional chemical synthesis (in solid phase or in homogeneous liquid phase), or by enzymatic synthesis (Kullman et al., J. Biol. Chem. 1980, 225, 8234), from constituent amino acids or their derivatives.

The peptide according to the invention may be of natural or synthetic origin. Preferentially according to the invention, the peptide is obtained by chemical synthesis.

According to the invention, the active principle may be a single peptide, a mixture of peptides or peptide derivatives and/or constituted of amino acid derivatives.

According to the invention, said peptide or mixture of peptides may be utilized as a medication.

The main object of the invention is a cosmetic or pharmaceutical composition comprising a peptide of general formula (I), characterized in that it is chosen from among sequences SEQ ID No. 1 to SEQ ID No. 10, in a physiologically suitable medium, as an active principle that activates human HMG-CoA reductase, alone or in combination with at least one other active principle.

The effective quantity of active principle corresponds to the quantity necessary to obtain the desired result, i.e., to activate the HMG-CoA reductase and inhibit the production of interleukin-1 type cellular mediators, and thus obtain a soothing effect in individuals presenting sensitive skin. According to certain aspects of the invention, the effective quantity of active principle is a quantity of peptide of general formula (I) sufficient for reducing or even eliminating an irritant cutaneous effect. Thus, this quantity is variable depending on the quantity and nature of the compound with an irritant character utilized and/or on the sensitivity of the user to this compound.

According to an advantageous embodiment of the invention, the active principle according to the invention is present in compositions of the invention at a concentration of between approximately 0.0005 and 500 ppm (parts per million). Preferentially, the active principle is present at a concentration of between approximately 0.01 and 5 ppm with relation to the total weight of the final composition.

According to an advantageous embodiment of the invention, the active principle according to the invention is previously solubilized in one or more physiologically acceptable solvents, conventionally used by the person skilled in the art, such as water, glycerol, ethanol, propylene glycol, butylene glycol, dipropylene glycol, ethoxylated diethylene glycol or propoxylated diethylene glycol, cyclic polyols, white petroleum jelly, vegetable oil or any mixture of these solvents.

According to another advantageous embodiment of the invention, the active principle according to the invention is previously solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

Of course, it is obvious that the invention is aimed at mammals in general, and more particularly at human beings.

The usable composition according to the invention may in particular consist of a composition for hair care, and notably a shampoo, a conditioner, a treatment lotion, a styling cream or gel, a hair restructuring lotion, a mask, etc. The cosmetic composition according to the invention may be notably used in treatments implementing an application that is followed or not followed by rinsing or else in shampoo form. Thus, the active principle according to the invention may advantageously be utilized in antidandruff care of the scalp. The active principle may also be present in the form of hair dye or mascara to be applied by brush or comb, in particular on the eyelashes, eyebrows or hair.

The active principle according to the invention may be utilized alone or rather in combination with at least one other active principle, in a cosmetic composition or for the preparation of a pharmaceutical and more particularly a dermatological composition.

Thus, the usable compositions according to the invention may also contain various active principles intended to promote the action of the active principle according to the invention. In a non-limiting manner, the following classes of ingredients may be cited: Other peptide active agents, vegetable extracts, cicatrizant, anti-age, anti-wrinkle, soothing, anti-radical, anti-UV agents, agents stimulating the synthesis of dermic macromolecules or energy metabolism, moisturizing, antibacterial, antifungal, anti-inflammatory, anesthetic agents, agents modulating cutaneous differentiation, pigmentation or depigmentation, agents stimulating nail or hair growth. Preferentially, an anti-radical or antioxidant agent will be utilized.

According to another aspect of the invention, the compositions may also comprise active principles with an irritant side effect that are thus likely to cause skin irritation, especially in persons with sensitive skin. As active principles that are likely to have an irritant side effect, the following may be cited, for example: keratolytic agents such as a-hydroxy-acids like glycolic, lactic, malic, citric, tartaric, mandelic acids and their derivatives; ss-hydroxy-acids like salicylic acid and its derivatives; a-keto-acids like ascorbic acid or vitamin C and its derivatives; retinoids like retinol and its esters, retinal, retinoic acid and its derivatives; minoxidil and its derivatives; lithium salts; hair tints or dyes like para-phenylenediamine (p-PDA) and some of its derivatives such as N-phenyl p-PDA and toluene 2,5-diamine sulfate; meta-phenylene diamine (m-PDA) and some of its derivatives such as toluene 3,4-diamine; ortho-phenylene diamine (o-PDA); alcoholic fragrancing solutions (perfume, eau de toilette, after shave, deodorant); anti-perspirant agents (certain aluminum salts); depilatory or permanent active ingredients (thiols, ammonium hydroxide); depigmenting agents (hydroquinone): anti-lice active ingredients; detergent (ionic and non-ionic) agents; And their mixtures.

Thus, according to this aspect of the invention, the peptide of general sequence (I) will be utilized as an active principle to prevent or combat skin irritations caused by the irritant active principle.

The compositions according to the invention will be applied by any appropriate route, notably oral, parenteral or external topical, and their formulations will be adapted by the person skilled in the art, in particular for cosmetic or pharmaceutical compositions. Advantageously, the compositions according to the invention are intended for topical administration on the skin. These compositions therefore must contain a physiologically acceptable medium, i.e., a medium compatible with the skin and epithelial appendages, and must cover all cosmetic or dermatological forms. These compositions will notably be in the form of creams, oil in water emulsions, or water in oil emulsions or multiple emulsions, solutions, suspensions, gels, milks, lotions, sticks or else powders, and suitable for an application on the skin, lips and/or epithelial appendages. These compositions comprise the excipients necessary for their formulation, such as solvents, thickeners, diluents, surface active agents, antioxidants, colorants, preservatives and fragrances.

According to another embodiment of the invention, the compositions will be appropriate for oral administration for pharmaceutical use. Thus, the compositions may in particular be present in the form of tablets, capsules, gel capsules, chewable pastes, powders to consume as is or to be mixed immediately before use with a liquid, syrups, gels or any other form known to the person skilled in the art. They will contain suitable formulation excipients, such as colorants, sweeteners, flavorings, bulking agents, binders and preservatives.

These compositions may particularly be present in the form of an aqueous solution, hydroalcoholic or oily solution; an oil in water emulsion, water in oil emulsion or multiple emulsions; They may also be present in the form of creams, suspensions or else powders, suitable for application on the skin, mucous membranes, lips and/or epithelial appendages. These compositions may be more or less fluid and have the appearance of a cream, lotion, milk, serum, pomade, gel, paste or foam. They may also be present in solid form, such as a stick, or may be applied on the skin in aerosol form. They may be utilized as a care product and/or as a skin makeup product.

These compositions also comprise any additive commonly utilized in the contemplated field of application as well as the adjuvants necessary for their formulation, such as solvents, thickeners, diluents, antioxidants, colorants, sunscreens, self-tanning agents, pigments, fillers, preservatives, fragrances, odor absorbers, cosmetic or pharmaceutical active ingredients, essential oils, vitamins, essential fatty acids, surface active agents, film-forming polymers, etc.

In all cases, the person skilled in the art will make sure that these adjuvants as well as their proportions are chosen so as to not harm the desired advantageous properties of the composition according to the invention. These adjuvants may, for example, correspond to 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

Another object of the invention is the utilization of an effective quantity of peptide of general formula (I), as an active principle soothing sensitive skin in a cosmetic composition.

Another object of the invention is the utilization of an effective quantity of peptide of general formula (I), as an active principle, in a cosmetic composition, to soothe sensitive skin.

Another object of the invention is the utilization of an effective quantity of peptide of general formula (I), in a cosmetic composition, to protect the skin from external stresses.

The expression "external stress" is understood to refer to stresses that the environment may produce. By way of example, one may cite stresses such as pollution, UV (ultraviolet radiation), oxidants, or else products with an irritant character such as surface active agents, preservatives, fragrances, or some active principles utilized in dermato-cosmetology, such as keratolytic active ingredients, exfoliants, alpha-hydroxy-acids (particularly lactic, glycolic, citric acids), 3-hydroxy-acids (particularly salicylic, n-octanoyl-5-salicylic acids) and retinoids (particularly retinol and its esters), and anti-lice active ingredients. Mechanical stresses such as abrasions, shaving or epilation may also be cited. Extreme climactic conditions are also an important cause of skin stress.

In particular, the object of the invention is the utilization of a cosmetic composition comprising an effective quantity of peptide according to the invention to prevent or treat damage caused to the skin by mechanical treatments such as shaving or epilation.

In particular, the object of the invention is the utilization of a cosmetic composition comprising an effective quantity of peptide according to the invention to prevent or treat damage caused to the skin by extreme climactic conditions or sudden variations in temperatures and hygrometry.

In particular, the object of the invention is the utilization of a cosmetic composition comprising an effective quantity of peptide according to the invention to prevent or treat damage caused to the skin by detergents causing a stripping effect on the epidermis.

In particular, the object of the invention is the utilization of a cosmetic composition comprising an effective quantity of peptide according to the invention to prevent or treat damage caused to the skin by UVB radiation.

In particular, the object of the invention is the utilization of a cosmetic composition comprising an effective quantity of peptide according to the invention to prevent or treat damage caused to the skin by oxidants.

The invention also consists of the utilization of the peptide according to the invention for preparing a pharmaceutical composition intended to prevent or treat cutaneous inflammation, such as erythema, in particular due to ultraviolet radiation, pruritus, urticaria, insect bites, allergies, or else alopecia in its inflammatory phases.

The invention further consists of a cosmetic treatment method intended to prevent and/or combat external stresses according to which a composition comprising an effective quantity of peptide according to the invention is applied onto the areas to be treated.

The invention further applies to a cosmetic treatment method intended to reduce or eliminate the irritant side effect of an active principle present in a cosmetic composition, characterized in that a composition comprising an effective quantity of the active principle according to the invention is applied topically onto the skin to be treated.

Particular embodiments of this cosmetic treatment method also result from the previous description. Other advantages and characteristics of the invention will more clearly appear upon reading the examples given for illustrative and non-limiting purposes.

EXAMPLE 1

Study of the Expression of HMG-CoA Reductase in Normal Human Keratinocytes in the Presence of Peptide SEQ ID No. 5

The goal of this study is to determine the influence of peptide SEQ ID No. 5 on the expression of HMG-CoA reductase in normal human keratinocytes.

Protocol:

Normal human keratinocytes in culture are treated with a 1% stock solution at 50 ppm of peptide SEQ ID No. 5 for 24 or 48 hours (the medium in the presence of the active ingredient is changed every 24 hours). The cells are then washed and fixed in cold methanol for 4 minutes at 4° C. The cells are incubated in the presence of a polyclonal rabbit antibody specific for HMG-CoA reductase (Millipore, Upstate), and then a secondary antibody coupled with a fluorescent dye. The cells are then examined by epifluorescence microscope (Nikon Eclipse E600 microscope).

Results:

Microscopic observations show more intense cytoplasmic fluorescence in cells treated by peptide SEQ ID No. 5.

Conclusion:

Peptide SEQ ID No. 5, at the 0.5 ppm concentration, stimulates the expression of HMG-CoA reductase in normal human keratinocytes.

EXAMPLE 2

Study of the Protective Effect of Peptide SEQ ID No. 4 on Skin Cells Subjected to Oxidative Stress The goal of this study is to determine the protective effect of peptide SEQ ID No. 4 in relation to normal human keratinocytes subjected to oxidative stress, caused by hydrogen peroxide solution ($H_2O_2$) at 2 mM. To do this, cellular viability tests were carried out by the MTT technique.

Protocol:

The normal human keratinocytes are treated with a 1% stock solution at 50 ppm of peptide SEQ ID No. 4, for 24 hours, subjected to oxidative stress caused by $H_2O_2$ at 2 mM for 30 minutes and then cultivated again 24 hours in the presence of the same concentration of peptide SEQ ID No. 4. Controls untreated by the peptide are carried out under the same conditions. At the end of the experiment, the cells are incubated in a solution containing 0.1 mg/ml of MTT (3-[4,5-dimethylthiazol-2-yl]-2,5-diphenyltetrazolium bromide), according to the protocol described in example 2.

Results:

Evaluation of cellular viability by the MTT technique shows that peptide SEQ ID No. 4 increases cellular viability of normal human keratinocytes by 13%.

Conclusion:

Peptide SEQ ID No. 4, at the 0.5 ppm concentration, effectively protects the skin cells from the cytotoxic effects of oxidative stress.

EXAMPLE 3

Study of the Protective Effect of Peptide SEQ ID No. 5 on Skin Cells Attacked by a Detergent The goal of this study is to determine the protective effect of peptide SEQ ID No. 5 with relation to normal human keratinocytes attacked by a detergent, in particular SDS. To do this, cellular viability tests were conducted by the MTT technique.

Protocol:

The normal human keratinocytes are treated with a 1% stock solution at 50 ppm of peptide SEQ ID No. 5, for 24 hours, subjected to contact with SDS at 15 µg/ml for 24 hours in the presence of the same concentration of peptide SEQ ID No. 5. Controls untreated by the peptide are carried out under the same conditions. At the end of the experiment, the cells are incubated in a solution containing 0.1 mg/ml of MTT (3-[4,5-dimethylthiazol-2-yl]-2,5-diphenyltetrazolium bromide), according to the protocol described in example 2.

Results:

Evaluation of cellular viability by the MTT technique shows that peptide SEQ ID No. 5 increases cellular viability of normal human keratinocytes by 18%.

Conclusion:

Peptide SEQ ID No. 5, at the 0.5 ppm concentration, effectively protects the skin cells from attack by an SDS type detergent.

EXAMPLE 4

Study of the Protective Effect of Peptide SEQ ID No. 5 on Skin Cells Subjected to Ultraviolet Radiation (UVB)

The goal of this study is to determine the protective effect of peptide SEQ ID No. 5 with relation to normal human keratinocytes subjected to stress by UVB radiation. To do this, cellular viability tests were conducted by the MTT technique.

Protocol:

The normal human keratinocytes are treated with a 1% solution, a solution at 50 ppm of peptide SEQ ID No. 5, for 24 hours, irradiated by UVB (50 mJ/cm$^2$) and then cultivated again 24 hours in the presence of the same concentration of peptide SEQ ID No. 5. Untreated and non-irradiated controls are carried out under the same conditions. At the end of the experiment, the cells are incubated in a solution containing 0.1 mg/ml of MTT (3-[4,5-dimethylthiazol-2-yl]-2,5-diphenyltetrazolium bromide). This compound is absorbed by the living cells and then metabolized by mitochondrial enzymes into a blue violet compound, formazan, that will be assayed by spectrophotometry at 540 nm. The optical density (O.D.) is then directly proportional to the mitochondrial enzymatic activity as well as to the number of living cells.

Results:

Evaluation of cellular viability by the MTT technique shows that peptide SEQ ID No. 5 increases cellular viability after UVB irradiation by 16%.

Conclusion:

Peptide SEQ ID No. 5, at the 0.5 ppm concentration, increases cellular viability and effectively protects the skin cells from the cytotoxic effects of UVB radiation.

EXAMPLE 5

Ex Vivo Study of the Effect of Peptide SEQ ID No. 5 on Interleukin-I (IL-1 Alpha) Secretion by Human Skin Biopsies The goal of this study is to determine the ex vivo effect of peptide SEQ ID No. 5 on the production of the IL-1 alpha cellular inflammation mediator by biopsies of human skin cultivated under standard conditions or subjected to stress by UVB radiation or SDS.

Protocol:

5 mm-diameter biopsies of human skin are maintained in culture at the air-liquid interface in the presence of standard culture medium. The samples are treated with a 1% dilution of a solution at 50 ppm of peptide SEQ ID No. 5 for 24 hours, and then irradiated by UVB radiation (200 mJ/cm$^2$) and put back in culture for 24 hours, or subjected to contact with SDS at 2.5% for 24 hours in the presence of the same concentration of peptide SEQ ID No. 5. Controls untreated by the peptide are carried out under the same conditions. At the end of the experiment, the quantity of interleukin-1 alpha salted out in the culture medium is assayed by the ELISA technique.

Results:

The quantity of IL-1 alpha salted out by the skin biopsies after a UVB radiation or SDS stress is significantly reduced (less 40% and less 58% respectively), if the samples have been treated with peptide SEQ ID No. 5.

Conclusion:

Peptide SEQ ID No. 5, at the 0.5 ppm concentration, significantly reduces the inflammation induced by UBV radiation or SDS detergent.

EXAMPLE 6

Preparation of Compositions

1—Sun Protection Cream:

| Trade names | INCI names | Weight percent |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoylmethane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Peptide SEQ ID No. 4 | | 3 ppm |
| Fragrance | Fragrance | qsp |
| Colorant | | qsp |

The constituents of phase A and phase B are heated separately between 70° C. and 75° C. Phase B is emulsified in phase A under stirring. Phase C is added at 45° C., by increasing the stirring. Phase D is then added when the temperature is below 40° C. The cooling is continued until 25° C. under intensive stirring.

2—After-Sun Lotion:

| Trade names | INCI names | Weight percent |
|---|---|---|
| PHASE A | | |
| Montanov L | C14-22 Alcohols (and) C12-20 Alkyl Glucoside | 3.00 |
| Waglinol 2559 | Cetearyl Isononanoate | 4.00 |
| Tegosoft TN | C12-15 Alkyl Benzoate | 3.00 |
| Apricot kernel oil | Prunus Armeniaca (Apricot) Kernel Oil | 2.00 |
| Avocado oil | Persea Gratissima (Avocado) Oil | 1.00 |
| Abil 350 | Dimethicone | 1.00 |
| PHASE B | | |
| Demineralized water | Aqua (Water) | qsp |
| PHASE C | | |
| Simulgel EG | Sodium Acrylate/Acryloyldimethyl Taurate Copolymer (and) Isohexadecane (and) Polysorbate 80 Copolymer (and) Polysorbate 80 | 0.4 |
| PHASE D | | |
| Phenonip | Phenoxyethanol (and) Methylparaben (and) Ethylparaben (and) Butylparaben (and) Propylparaben (and) Isobutylparaben Ethylparaben and Propylparaben and Butylparaben | 0.30 |
| Germall 115 | Imidazolidinyl Urea | 0.20 |
| PHASE E | | |
| Peptide SEQ ID No. 5 | | 0.1 ppm |

Prepare phase A under stirring. Progressively incorporate the xanthan gum, under deflocculating stirring. Phases C and D will be incorporated once the gel is finished. Phase E, prepared previously until the DHA is completely dissolved, will then be added. If necessary, adjust the pH to 4-4.5. Add color and fragrance.

3—Protective Day Cream:

| Trade names | INCI names | Weight percent |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qsp 100 |
| Glycerin | Glycerin | 2.00 |
| Carbopol EDT 2020 | Acrylates/C10-30 Alkyl Acrylate Crosspolymer | 0.15 |
| Keltrol BT | Xanthan Gum | 0.30 |
| Phase C | | |
| Sodium Hydroxide (10% oil) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| Peptide SEQ ID No. 5 | | 5 ppm |

Prepare phase A and heat to 75° C. under stirring. Prepare phase B by dispersing the carbopol and then the xanthan gum under stirring. Let rest. Heat to 75° C.

At temperature, emulsify A into B under rotor stator stirring. Neutralize with phase C under rapid stirring. After cooling to 40° C., add phase D, and then phase E. Cooling is continued under mild stirring and phase F is added.

Applicants incorporate by reference the material contained in the accompanying computer readable Sequence Listing entitled "US08-113_SEQUENCE_LISTING.txt", which was created on Sep. 20, 2011, and is 2,147 bytes in size, and hereby confirm that the information recorded in the computer readable form is identical to the written sequence listing.

The invention claimed is:

1. A cosmetic composition comprising: a peptide that activates human HMG-CoA reductase, alone or in combination with at least one other active principle, wherein the peptide is selected from the group consisting of:

```
                                        (SEQ ID NO. 1)
Glu-Gly-Lys-Gly-Lys-Ser-Val-Val-Cys-Glu, (SEQ ID NO. 2)
Glu-Gly-Lys-Gly-Lys-Ser-Val-Val, (SEQ ID NO. 3)
Asp-Gly-Lys-Gly-Lys-Thr, (SEQ ID NO. 4)
Arg-Gly-Lys-Ser, (SEQ ID NO. 5)
Arg-Gly-Lys-Ser-NH₂, (SEQ ID NO. 6)
Arg-Gly-Lys-Thr, (SEQ ID NO. 7)
Arg-Gly-Lys-Thr-NH₂, (SEQ ID NO. 8)
Lys-Gly-Lys-Ser, (SEQ ID NO. 9)
Lys-Gly-Lys-Ser-NH₂, and (SEQ ID NO. 10)
Gly-Lys-Ser-NH₂; and
``` a cosmetically suitable medium.

2. The composition according to claim 1 wherein said peptide corresponds to the SEQ ID NO: 4 sequence.

3. The composition according to claim 1 wherein said peptide corresponds to the SEQ ID NO: 5 sequence.

4. The composition according to claim 1, wherein said peptide is present at a concentration of between 0.0005 and 500 ppm.

5. The composition according to claim 4, wherein said peptide is present at a concentration of between 0.01 and 5 ppm.

6. The composition according to claim 1, wherein the composition is a topically administrable composition.

7. The composition according to claim 1, wherein the composition contains at least one other active promoting the action of said peptide, wherein the active is selected from the group consisting of other peptide active agents, vegetable extracts, cicatrizant, anti-aging agents, anti-wrinkle agents, soothing agents, anti-radical agents, anti-UV agents, agents stimulating the synthesis of dermic macromolecules or energy metabolism, moisturizing agents, antibacterial agents, antifungal agents, anti-inflammatory agents, anesthetic agents, agents modulating cutaneous differentiation, pigmentation or depigmentation, agents stimulating nail or hair growth, antioxidant agents, and combinations thereof.

8. The composition according to claim 1, wherein the composition also contains at least one other active principle with an irritant side effect.

9. The composition according to claim 1, wherein said peptide is solubilized in one or more physiologically acceptable solvents selected from the group consisting of water, glycerol, ethanol, propylene glycol, butylene glycol, dipropylene glycol, ethoxylated diethylene glycol or propoxylated diethylene glycol, cyclic polyols, white petroleum jelly, vegetable oil and combinations thereof.

10. The composition according to claim 1, wherein the composition is a cosmetic composition comprising an effective quantity of the peptide as a soothing active principle.

11. The composition according to claim 10, wherein the peptide is present in an effective quantity to protect the skin from external stresses.

12. The composition according to claim 11, wherein the external stresses are UVB radiation or oxidants.

13. The composition according to claim 10, wherein the peptide is present in an effective quantity for soothing sensitive skin.

14. A cosmetic treatment method for the reduction and elimination of the irritant side effect of a compound present in a cosmetic composition, the method comprising topically applying, to skin to be treated, a composition comprising an effective quantity of a peptide derived from human HMG-CoA reductase selected from the group consisting of:

```
                                        (SEQ ID NO. 1)
Glu-Gly-Lys-Gly-Lys-Ser-Val-Val-Cys-Glu, (SEQ ID NO. 2)
Glu-Gly-Lys-Gly-Lys-Ser-Val-Val, (SEQ ID NO. 3)
Asp-Gly-Lys-Gly-Lys-Thr, (SEQ ID NO. 4)
Arg-Gly-Lys-Ser, (SEQ ID NO. 5)
Arg-Gly-Lys-Ser-NH₂

(SEQ ID NO. 6)
Arg-Gly-Lys-Thr, (SEQ ID NO. 7)
Arg-Gly-Lys-Thr-NH₂, (SEQ ID NO. 8)
Lys-Gly-Lys-Ser, (SEQ ID NO. 9)
Lys-Gly-Lys-Ser-NH₂, and (SEQ ID NO. 10)
Gly-Lys-Ser-NH₂; and
``` a cosmetically suitable medium.

15. The method according to claim 14, wherein the peptide corresponds to the SEQ ID NO: 4 sequence.

16. The method according to claim 14, wherein the peptide corresponds to the SEQ ID NO: 5 sequence.

17. The method according to claim 14, wherein said peptide is present at a concentration of between 0.0005 and 500 ppm.

18. The method according to claim 14, wherein said peptide is solubilized in one or more physiologically acceptable solvents selected from the group consisting of water, glycerol, ethanol, propylene glycol, butylene glycol, dipropylene glycol, ethoxylated diethylene glycol or propoxylated diethylene glycol, cyclic polyols, white petroleum jelly, vegetable oil and combinations thereof.

* * * * *